(12) United States Patent
Haskell

(10) Patent No.: US 6,814,319 B2
(45) Date of Patent: Nov. 9, 2004

(54) LABORATORY SCALE MILLING PROCESS

(75) Inventor: Royal J. Haskell, Kalamazoo, MI (US)

(73) Assignee: Pharmacia & Upjohn Company, Kalamazoo, MI (US)

( * ) Notice: Subject to any disclaimer, the term of this patent is extended or adjusted under 35 U.S.C. 154(b) by 54 days.

(21) Appl. No.: 10/007,515

(22) Filed: Dec. 5, 2001

(65) Prior Publication Data

US 2002/0119200 A1 Aug. 29, 2002

Related U.S. Application Data

(60) Provisional application No. 60/251,750, filed on Dec. 6, 2000.

(51) Int. Cl.[7] ............................................. B02C 19/12
(52) U.S. Cl. ..................................................... 241/21
(58) Field of Search ..................... 424/489; 264/15; 366/274; 241/171, 172, 21

(56) References Cited

U.S. PATENT DOCUMENTS

| | | | |
|---|---|---|---|
| 3,245,665 A | 4/1966 | Steel | 259/144 |
| 4,477,192 A | 10/1984 | Bonney | 366/274 |
| 4,498,785 A | 2/1985 | de Bruyne | 366/274 |
| 4,676,439 A | 6/1987 | Saito et al. | 241/172 |
| 4,837,114 A | 6/1989 | Hamada et al. | 427/127 |
| 5,145,684 A | 9/1992 | Liversidge et al. | 424/489 |
| 5,298,262 A | 3/1994 | Na et al. | 424/489 |
| 5,302,401 A | 4/1994 | Liversidge et al. | 424/501 |
| 5,336,507 A | 8/1994 | Na et al. | 424/489 |
| 5,340,564 A | 8/1994 | Illig et al. | 424/9 |
| 5,346,702 A | 9/1994 | Na et al. | 424/490 |
| 5,352,459 A | 10/1994 | Hollister et al. | 424/489 |
| 5,429,824 A | 7/1995 | June | 424/489 |
| 5,470,401 A | 11/1995 | McCallum et al. | 148/302 |
| 5,503,723 A | 4/1996 | Ruddy et al. | 204/450 |
| 5,510,118 A | 4/1996 | Bosch et al. | 424/489 |
| 5,534,270 A | 7/1996 | De Castro | 424/490 |
| 5,552,160 A | 9/1996 | Liversidge et al. | 424/489 |
| 5,573,783 A | 11/1996 | Desieno et al. | 424/490 |
| 5,585,108 A | 12/1996 | Ruddy et al. | 424/434 |
| 5,586,823 A | 12/1996 | Carr | 366/274 |
| 5,591,456 A | 1/1997 | Franson et al. | 424/494 |

(List continued on next page.)

FOREIGN PATENT DOCUMENTS

| | | |
|---|---|---|
| DE | 34 07 608 | 9/1984 |
| EP | 0 531 988 | 3/1993 |
| WO | WO 91/04810 | 4/1991 |

OTHER PUBLICATIONS http://www.indigoinstruments.com/magnets/gphmgnts/rare-earth-magnets.html. Neodymium Rare Earth Magnets.
http://www.magtec.com/magtec01-1.html. Magtec Products.
http://www.magnetsource.com/rearth.htm. Rare Earth Magnets.
Lieberman et al., ed. *Pharmaceutical Dosage Forms: Tablets*, vol. 1, 2nd ed., Marcel Dekker, 34–36. (1989).
Lieberman et al., ed. *Pharmaceutical Dosage Forms: Tablets*, vol. 2, 2nd ed., Marcel Dekker, 107–113 (1989).
United States Pharmacopeia, 24th ed., 2254–2304. (2000).

*Primary Examiner*—Mark Rosenbaum
(74) *Attorney, Agent, or Firm*—Mary J. Hosley

(57) ABSTRACT

There is provided a process for reducing particle size of a drug, the process comprising (a) a step of dispersing about 10 g or less of the drug in a suitable volume of a liquid dispersion medium to form a suspension; (b) a step of bringing together in a vessel grinding media, magnetically activatable means for stirring and the suspension; (c) a step of magnetically activating the means for stirring to effect milling of the suspension to a weight average particle size not greater than about 1 μm; and (d) a step of separating the resulting milled suspension from the grinding media and the magnetically activatable means for stirring.

49 Claims, 4 Drawing Sheets

U.S. PATENT DOCUMENTS

| | | |
|---|---|---|
| 5,662,883 A | 9/1997 | Bagchi et al. ................ 424/9.4 |
| 5,665,331 A | 9/1997 | Bagchi et al. ............. 424/9.45 |
| 5,676,462 A | 10/1997 | Fraczek et al. .......... 366/171.1 |
| 5,711,912 A | 1/1998 | Chatterjee et al. .......... 264/428 |
| 5,934,579 A * | 8/1999 | Hiersche et al. ............... 241/65 |
| 5,958,822 A | 9/1999 | Beckerbauer et al. ....... 502/168 |
| 5,967,430 A * | 10/1999 | Getzmann .................... 241/29 |
| 2002/0179758 A1 * | 12/2002 | Reed et al. ................. 241/172 |

* cited by examiner

LABORATORY SCALE MILLING PROCESS

This application claims priority of U.S. provisional application Ser. No. 60/251,750 filed on Dec. 6, 2000.

FIELD OF THE INVENTION

The present invention relates to a process for milling drugs on a small scale and to use of drugs milled by such a process in manufacture of medicaments.

BACKGROUND OF THE INVENTION

The bioavailability of an orally administered drug, as measured by its entry into systemic circulation in the bloodstream, depends on at least two fundamental processes: drug dissolution in gastrointestinal fluids (in vivo drug release) and subsequent absorption of the dissolved drug. Several factors influence dissolution of a drug from its carrier, including surface area of the drug presented to the dissolution solvent medium, solubility of the drug substance in the specific solvent medium, and driving forces of the saturation concentration of dissolved materials in the solvent medium. Notwithstanding these factors, a strong correlation has been established between the in vitro dissolution time determined by standard assay procedures for an oral dosage form and the rate of in vivo drug release. This correlation is so firmly established in the art that dissolution time has become generally descriptive of drug release potential for the active component of the particular dosage form.

When the process of in vivo drug release is slower than the process of absorption, absorption is said to be dissolution rate-limited. Since dissolution precedes absorption in the overall process, any change in the drug release or dissolution process will subsequently influence drug absorption. See for example Lieberman et al. (1989), *Pharmaceutical Dosage Forms: Tablets*, Vol. 1, pp. 34–36. Marcel Dekker, New York. It is clear, therefore, that dissolution time determined for a composition is one of the important fundamental characteristics for consideration when evaluating compositions intended for rapid-onset delivery, particularly where drug absorption is dissolution rate-limited.

It is well known that one way to improve dissolution of drugs of low water solubility is to reduce drug particle size thereby increasing the specific surface area of the drug. Indeed, patent and other literature relating to nanoparticulate drug compositions teaches that, in general, the smaller the drug particle size, the greater is the advantage in speed of onset of therapeutic effect, or other pharmacodynamic benefit, obtained upon oral administration. For example, at least the following patents propose reduction of particle size to about 400 nm or smaller.

U.S. Pat. No. 5,145,684 to Liversidge et al.
U.S. Pat. No. 5,298,262 to Na & Rajagopalan.
U.S. Pat. No. 5,302,401 to Liversidge et al.
U.S. Pat. No. 5,336,507 to Na & Rajagopalan.
U.S. Pat. No. 5,340,564 to Illig & Sarpotdar.
U.S. Pat. No. 5,346,702 to Na & Rajagopalan.
U.S. Pat. No. 5,352,459 to Hollister et al.
U.S. Pat. No. 5,429,824 to June.
U.S. Pat. No. 5,503,723 to Ruddy et al.
U.S. Pat. No. 5,510,118 to Bosch et al.
U.S. Pat. No. 5,534,270 to De Castro.
U.S. Pat. No. 5,552,160 to Liversidge et al.
U.S. Pat. No. 5,573,783 to Desieno & Stetsko.
U.S. Pat. No. 5,585,108 to Ruddy et al.
U.S. Pat. No. 5,591,456 to Franson et al.
U.S. Pat. No. 5,662,883 to Bagchi et al.
U.S. Pat. No. 5,665,331 to Bagchi et al.

Mills are among the most commonly used kinds of particle size reduction equipment for preparation of drugs and drug compositions. While there are many different types of mills, most have at least three basic components in common: (1) a structure for feeding material into the mill, (2) a milling chamber with working parts, and (3) a take-off to a receiver or collector in which the milled product is deposited. See Lieberman et al. (1989), op. cit., Vol. 2., p. 113. Non-limiting examples of mills commonly used to prepare and process drugs include fluid energy mills, ball or rod mills, hammer mills, cutting mills, oscillating granular mills, wet mills, high energy mills, etc.

Although, as described above, dissolution and bioavailability advantages can be realized by milling drugs, particularly drugs of low water solubility, to smaller particle sizes, many difficulties preclude use of known types of mills in certain situations. For example, no practical means of milling small amounts (e.g., less than about 10 grams) of drug material to nanoparticulate dimensions, i.e., to particle sizes smaller than about 1 $\mu$m, have hitherto been available. This has made the entire approach of preparing nanoparticulate drugs (either suspensions or solid compositions), for the purpose of studying enhancement of dissolution, inaccessible for new drugs in discovery and early development phases, and for cold- or radioactively-labeled drugs— situations in which the quantity of drug available for such studies is usually very limited. Consequently, development of important drug formulations, for example rapid-onset formulations, is often delayed until larger quantities of drug are available.

Additionally, milling is a very inefficient unit operation with only approximately 0.05% to 2% of the applied energy being utilized in the actual reduction of particle size. Although milling efficiency is dependent upon the type of mill and the characteristic of the material being milled, in general, a large portion (e.g., about 10% to about 50%) of the energy expended during milling is converted to heat. This heat is generated by friction of particles contacting the mill, by plastic deformation of particles that are not fractured, by friction of particles colliding with each other, and/or by friction of mechanical mill parts, etc. In many instances, this heat generation leads to drug degradation. Consequently, common milling processes are suitable only for drugs which are thermally stable. Alternatively, expensive heat removal equipment must be employed to maintain drug stability.

A further difficulty is that traditional milling equipment suitable for particle size reduction to less than 1 $\mu$m is generally very expensive and as such, is not widely available. Moreover, given the complexity of size reduction processes, few theories of general applicability have been developed. Therefore, most size reduction problems in the pharmaceutical industry must be solved empirically rather than theoretically. See Lieberman et al. (1989), op. cit., Vol. 2., pp. 107–112. Even when available, traditional milling equipment designed for heavy industry or large scale use is often not amenable to small scale empirical problem solving.

A yet further difficulty with traditional milling is that steel or some similar grinding media are typically employed. Use of metals in milling a suspension introduces the risk of metal contamination and consequent chemical decomposition.

Therefore, if an inexpensive, widely available, energy-efficient, laboratory-scale process for milling drugs of low water solubility to a nanoparticulate size range could be developed, a significant advance would be realized in preparation of drugs and drug compositions used in the treatment of a wide variety of disorders, particularly disorders where rapid onset of therapeutic action is desired.

SUMMARY OF THE INVENTION

Accordingly, the present invention provides a process for reducing particle size of a drug, the process comprising (a) a step of dispersing about 10 g or less of the drug in a suitable volume of a liquid dispersion medium to form a suspension; (b) a step of bringing together in a vessel grinding media, magnetically activatable means for stirring and the suspension; (c) a step of magnetically activating the means for stirring to effect milling of the suspension to a weight average particle size not greater than about 1 $\mu$m; and (d) a step of separating the resulting milled suspension from the grinding media and the magnetically activatable means for stirring.

In one embodiment of the invention, the process further comprises (e) a step of drying the milled suspension resulting from step (c) to form a drug powder. In this embodiment, the drying step (e) can occur prior to or after step (d). Drug powders prepared according to this process can be further formulated to provide a pharmaceutical composition.

Other features of the invention will be in part apparent and in part laid out hereinafter.

DETAILED DESCRIPTION OF THE INVENTION

Figure 1:
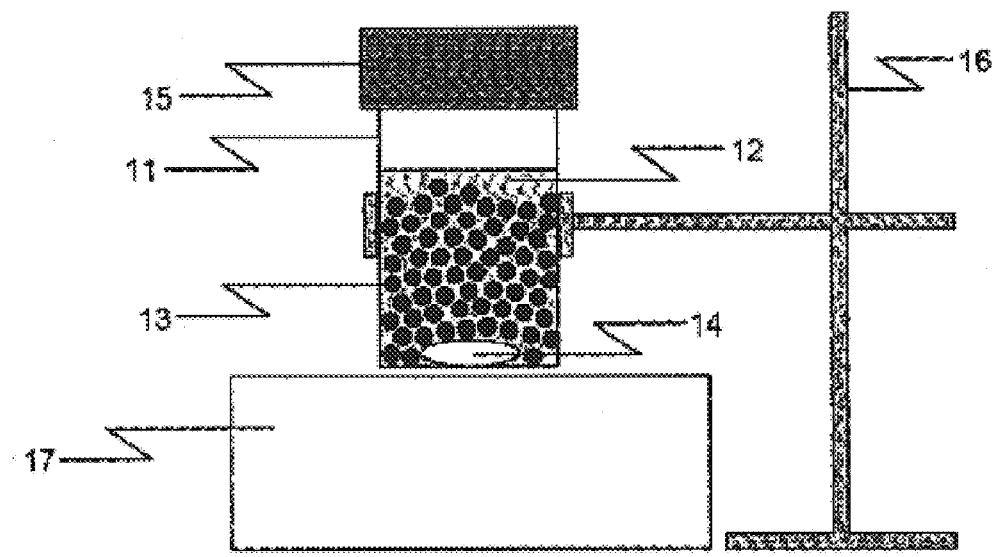
FIG. 1 shows in diagrammatic form an apparatus suitable for the process of the invention.

The process of the invention is especially suitable for reducing particle size of a drug of low water solubility. The process comprises (a) a step of dispersing about 10 g or less, preferably about 5 g or less, and more preferably about 2.5 g or less, of the drug in a suitable volume of a liquid dispersion medium to form a suspension; (b) a step of bringing together in a vessel grinding media, magnetically activatable means for stirring, and the suspension; (c) a step of magnetically activating the means for stirring to effect milling of the suspension to a $D_{50}$ particle size not greater than about 1 $\mu$m; and (d) a step of separating the resulting milled suspension from the grinding media and the magnetically activatable means for stirring.

Drugs of Low Water Solubility

Any suitable drug may be utilized in methods, processes and compositions of the invention. Preferably, the drug is one having low water solubility, for example a solubility in water, measured at 37° C., not greater than about 10 mg of drug per ml of water, and preferably not greater than about 1 mg of drug per ml of water. Solubility in water for many drugs can be readily determined from standard pharmaceutical reference books, for example *The Merck Index*, 11th ed., 1989 (published by Merck & Co., Inc., Rahway, N.J.); the *United States Pharmacopoeia*, 24th ed. (U.S. Pat. No. 24), 2000; *The Extra Pharmacopoeia*, 29th ed., 1989 (published by Pharmaceutical Press, London); and the *Physicians Desk Reference* (PDR), 2000 ed. (published by Medical Economics Co., Montvale, N.J.), each of which is individually incorporated herein by reference.

For example, individual drugs of low solubility as defined herein include those drugs categorized as "slightly soluble", "very slightly soluble", "practically insoluble" and "insoluble" in U.S. Pat. No. 24, pp. 2254–2298; and those drugs categorized as requiring 100 ml or more of water to dissolve 1 g of the drug, as listed in U.S.P. at 24, pp. 2299–2304. Processes of the invention are particularly suitable for drugs the absorption of which is dissolution-rate limited.

Illustratively, suitable drugs of low water solubility include, without limitation, drugs from the following classes: abortifacients, ACE inhibitors, α- and β-adrenergic agonists, α- and β-adrenergic blockers, adrenocortical suppressants, adrenocorticotropic hormones, alcohol deterrents, aldose reductase inhibitors, aldosterone antagonists, anabolics, analgesics (including narcotic and non-narcotic analgesics), androgens, angiotensin II receptor antagonists, anorexics, antacids, anthelminthics, antiacne agents, antiallergics, antialopecia agents, antiamebics, antiandrogens, antianginal agents, antiarrhythmics, antiarteriosclerotics, antiarthritic/antirheumatic agents (including selective COX-2 inhibitors), antiasthmatics, antibacterials, antibacterial adjuncts, anticholinergics, anticoagulants, anticonvulsants, antidepressants, antidiabetics, antidiarrheal agents, antidiuretics, antidotes to poison, antidyskinetics, antieczematics, antiemetics, antiestrogens, antifibrotics, antiflatulents, antifungals, antiglaucoma agents, antigonadotropins, antigout agents, antihistaminics, antihyperactives, antihyperlipoproteinemics, antihyperphosphatemics, antihypertensives, antihyperthyroid agents, antihypotensives, antihypothyroid agents, anti-inflammatories, antimalarials, antimanics, antimethemoglobinemics, antimigraine agents, antimuscarinics, antimycobacterials, antineoplastic agents and adjuncts, antineutropenics, antiosteoporotics, antipagetics, antiparkinsonian agents, antipheochromocytoma agents, antipneumocystis agents, antiprostatic hypertrophy agents, antiprotozoals, antipruritics, antipsoriatics, antipsychotics, antipyretics, antirickettsials, antiseborrheics, antiseptics/disinfectants, antispasmodics, antisyphylitics, antithrombocythemics, antithrombotics, antitussives, antiulceratives, antiurolithics, antivenins, antiviral agents, anxiolytics, aromatase inhibitors, astringents, benzodiazepine antagonists, bone resorption inhibitors, bradycardic agents, bradykinin antagonists, bronchodilators, calcium channel blockers, calcium regulators, carbonic anhydrase inhibitors, cardiotonics, CCK antagonists, chelating agents, cholelitholytic agents, choleretics, cholinergics, cholinesterase inhibitors, cholinesterase reactivators, CNS stimulants, contraceptives, debriding agents, decongestants, depigmentors, dermatitis herpetiformis suppressants, digestive aids, diuretics, dopamine receptor agonists, dopamine receptor antagonists, ectoparasiticides, emetics, enkephalinase inhibitors, enzymes, enzyme cofactors, estrogens, expectorants, fibrinogen receptor antagonists, fluoride supplements, gastric and pancreatic secretion stimulants, gastric cytoprotectants, gastric proton pump inhibitors, gastric secretion inhibitors, gastroprokinetics, glucocorticoids, α-glucosidase inhibitors, gonad-stimulating principles, growth hormone inhibitors, growth hormone releasing factors, growth stimulants, hematinics, hematopoietics, hemolytics, hemostatics, heparin antagonists, hepatic enzyme inducers, hepatoprotectants, histamine $H_2$ receptor antagonists, HIV protease inhibitors, HMG CoA reductase inhibitors, immunomodulators, immunosuppressants, insulin sensitizers, ion exchange resins, keratolytics, lactation stimulating hormones, laxatives/cathartics, leukotriene antagonists, LH-RH agonists, lipotropics, 5-lipoxygenase inhibitors, lupus erythematosus suppressants, matrix metalloproteinase inhibitors, mineralocorticoids, miotics, monoamine oxidase inhibitors, mucolytics, muscle relaxants, mydriatics, narcotic antagonists, neuroprotectives, nootropics, ovarian hormones, oxytocics, pepsin inhibitors, pigmentation agents, plasma volume expanders, potassium channel activators/openers, progestogens, prolactin inhibitors, prostaglandins, protease inhibitors, radio-pharmaceuticals, 5α-reductase inhibitors, respiratory stimulants, reverse transcriptase inhibitors, sedatives/hypnotics, serenics, serotonin noradrenaline reuptake inhibitors, serotonin receptor agonists, serotonin receptor antagonists, serotonin uptake inhibitors, somatostatin analogs, thrombolytics, thromboxane $A_2$ receptor antagonists, thyroid hormones, thyrotropic hormones, tocolytics, topoisomerase I annd II inhibitors, uricosurics, vasodilators, vasoprotectants, xanthine oxidase inhibitors, and combinations thereof.

Non-limiting illustrative examples of suitable drugs of low water solubility include acetohexamide, acetylsalicylic acid, alclofenac, allopurinol, atropine, benzthiazide, carbamazepine, carpofen, celecoxib, chlordiazepoxide, chlorpromazine, clonidine, codeine phosphate, codeine sulfate, codeine, deracoxib, diacerein, diclofenac, diltiazem, enolic acids, estradiol, etodolac, etoposide, fenbufen, fenclofenac, fenprofen, fentiazac, flurbiprofen, griseofulvin, haloperidol, ibuprofen, indomethacin, indomethacine, indoprofen, ketoprofen, linezolid, lorazepam, medroxyprogesterone acetate, megestrol, methoxsalen, methylprednisone, morphine sulfate, morphine, naproxen, nicergoline, nifedipine, niflumic, oxaprozin, oxazepam, oxyphenbutazone, parecoxib, phenindione, phenobarbital, phenytoin, piroxicam, pirprofen, prednisolone, prednisone, procaine, progesterone, pyrimethamine, rofecoxib, sulfadiazine, sulfamerazine, sulfisoxazole, sulindac, suprofen, temazepam, tiaprofenic acid, tilomisole, tolmetic, valdecoxib, etc.

Where the drug being milled is not of low water solubility, the liquid dispersion medium is preferably substantially free of water.

Energy Efficiency

A presently contemplated advantage of the process of the invention, in addition to its unique suitability where only small quantities of drug are available, is that it requires less energy and/or produces less heat than conventional milling processes. Consequently, the process of the invention results in substantially less or no drug degradation (and/or conversion of crystalline to amorphous state) compared to conventional milling processes, particularly where moderately stable or unstable drugs are used. Heat production can be measured by standard means, for example, by using a thermometer. Drug degradation and conversion to an amorphous state can be measured by any method known in the art, for example, by high performance liquid chromatography (HPLC), high pressure liquid chromatography, thin-layer chromatography (TLC), paper chromatography, gas chromatography, differential scanning calorimetry (DSC), X-ray crystallography, etc.

Chemical Stability

Another presently contemplated advantage of the process of the invention is that it employs chemically inert grinding media which are substantially resistant to chipping or cracking. Consequently, risk of chemical degradation of drug particles due to milling is greatly reduced or eliminated.

Drug Particle Size

As used herein, the term "$D_{50}$" refers to a linear measure of diameter having a value such that 50% by volume of particles in the formulation, in the longest dimension of the particles, are smaller than that diameter. For practical purposes a determination of $D_{50}$ based on 50% by weight rather than by volume is generally suitable. As used herein, therefore, $D_{50}$ particle size is essentially synonymous with weight average particle size.

Particle size can also be characterized, for example, by $D_{10}$, which refers to a linear measure of diameter having a value such that 10% by volume of particles in the formulation, in the longest dimension of the particles, are smaller than that diameter, or by $D_{90}$, which refers to a linear measure of diameter having a value such that 90% by volume of particles in the formulation, in the longest dimension of the particles, are smaller than that diameter.

Drugs prepared according to the process of the invention have a $D_{50}$ particle size not greater than about 1000 nm, preferably about 10 nm to about 1000 nm, more preferably about 100 nm to about 1000 nm, still more preferably about 400 nm to about 900 nm and most preferably about 500 nm to about 800 nm.

In a further preferred embodiment, about 50% to 100%, more preferably about 75% to 100%, and still more preferably about 90% to 100% by weight of drug particles prepared according to the process of the invention have a linear diameter not greater than about 1000 nm. In a particularly preferred embodiment, substantially all of the drug particles prepared by the process of the invention have a linear diameter not greater than about 1000 nm.

Any suitable detection method can be used to determine particle size of drugs prepared according to the process of the invention. Illustrative processes include appropriate microscopy (e.g. visible light microscopy, ultraviolet microscopy, or electron microscopy), dynamic light scattering (DLS), turbidimetry, etc. In general, one of ordinary skill in the art will be able to select an appropriate size detection method for the particle size range being detected.

Liquid Dispersion Medium

The invention can be practiced with any liquid dispersion medium in which the particular drug selected is substantially insoluble (i.e., less than about 10 and preferably less than about 1 mg of drug per ml of liquid dispersion medium). A presently preferred liquid dispersion medium is water. However, the invention can be practiced with other liquid dispersion media in which the particular drug selected is substantially insoluble, for example, aqueous salt solutions, safflower oil, and solvents such as ethanol, t-butanol, hexane and glycols. Alternatively, the liquid dispersion medium can comprise molten material, for example molten polyethylene glycol or a gelucire, which can be heated and maintained in liquid form during milling and then allowed to cool and solidify after milling.

A suitable liquid dispersion medium preferably comprises at least one surface modifying agents. Surface modifying agent(s) can be added to the liquid dispersion medium at any step of the process, for example, before and/or after the milling step (c). Preferably, surface modifying agent(s) are added prior to the milling step (c). Suitable surface modifying agents can be selected from known organic and inorganic pharmaceutically acceptable excipients. Such excipients include various polymers, low molecular weight oligomers, natural products, surfactants, etc. Non-limiting, representative examples of excipients that can be used as surface modifying agents include gelatin, casein, lecithin (phosphatides), gum acacia, cholesterol, tragacanth, stearic acid, benzalkonium chloride, calcium stearate, glyceryl monostearate, cetostearyl alcohol, cetamacrogol emulsifying wax, sorbitan esters, polyoxyethylene sorbitan fatty acid esters, polyoxyethylene castor oil derivatives, polyethylene glycols, polyoxyethylene stearates, colloidal silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethylcellulose, noncrystalline cellulose, magnesium aluminum silicate, triethanolamine, polyvinyl alcohol, and polyvinylpyrrolidone, preferably polyvinylpyrrolidone having a molecular weight of about 30,000. Most of these excipients are described in detail in *The Handbook of Pharmaceutical Excipients*, The Pharmaceutical Press (1986). Surface modifying agents are commercially available and/or can be prepared by processes known in the art.

Particularly preferred surface modifying agents are sodium dodecyl sulfate, polyvinylpyrrolidone, hydroxypropylcellulose and hydroxypropylmethylcellulose. If present in a liquid dispersion medium, at least one surface modifying agent is preferably present in a total amount of about 0.1% to about 90%, preferably about 0.1% to about 50%, and more preferably about 0.1% to about 25%, by weight based on the combined weight of drug and the at least one surface modifying agent.

For some drugs, particles will tend to agglomerate during the milling process of the invention. Without being bound by theory, it is believed that drug particle agglomeration during milling prevents reduction of drug particles to small sub-micron sizes. Where such small sub-micron particle sizes are desired, one or more surface modifying agents are preferably selected (by type and amount) so as to minimize, reduce and/or inhibit drug particle agglomeration during and/or after milling.

One of ordinary skill in the art will, through routine optimization, be able to determine which surface modifying agents (and ideal concentrations) are effective for minimizing, inhibiting, and/or reducing agglomeration of particles of a particular drug during milling and/or storage of the suspension. Illustratively, if particle agglomeration occurs during milling of a particular drug, a miniaturized screening assay can be performed to optimize liquid dispersion medium components. An exemplary miniaturized screening assay is a 96-well plate screen. Visual detection or automated absorbance can be used to measure drug particle agglomeration. Such an assay can also be used to optimize liquids used to rinse and/or dilute milled suspensions and to test drug particle agglomeration under stressed conditions such as freeze-thaw or elevated temperatures.

Conversely, where a lower limit on drug particle size reduction is desired (i.e. drug particles below a specific size are not desired) one of ordinary skill in the art will readily be able to control the use of surface modifying agents during milling so as to not limit drug particle agglomeration and, consequently, limit drug particle size reduction to the desired range.

Preferably, one or more antifoaming agents are added to the liquid dispersion medium. If present in a liquid dispersion medium, one or more antifoaming agents are typically present in a total amount of about 0.001% to about 2.5%, and preferably about 0.003% to about 1%, by weight of the liquid dispersion medium. Silicon-based polymers are preferred antifoaming agents. Polydimethylsiloxane (e.g. simethicone USP) and Sigma Antifoam A Concentrate or an equivalent thereof are particularly preferred antifoaming agents.

Preferably, the apparent viscosity of a liquid dispersion medium used to prepare nanoparticulate drug particles according to the invention is about 1 to about 1000 cP, and preferably about 1 to about 500 cP.

In the process of the invention, about 10 g or less of a drug is placed in a suitable amount of the liquid dispersion medium. What constitutes a "suitable amount" in the present context depends, among other factors, on the amount of drug used, the particular drug being used, the size of the vessel, the amount of grinding media used, and the particular components of the liquid dispersion medium. In general, a suitable amount of liquid dispersion medium is an amount which, after the drug is dispersed therein, results in a concentration of drug in the liquid dispersion medium of about 0.1% to about 90%, preferably about 5% to about 65%, and more preferably about 10% to about 50%, by weight. Concentrations can be readily optimized by one skilled in the art depending on the particular drug and the particular liquid dispersion medium used. Without being bound by theory, higher drug concentrations are generally desired and tend to result in a more efficient milling process and in more flexibility in transferring a suspension after milling. This in turn allows for increased recovery of milled drug particles.

Grinding Media

Grinding media of any suitable shape (e.g., balls, banded balls, cubes, cylinders, beads, etc.), size, size distribution, density and/or material can be used in the milling step. The grinding media should be chemically inert and resistant to chipping or cracking during the process of the invention. Preferred grinding media comprise glass, lead-free glass, latex and/or zirconium oxide and are in the shape of spherical beads. Preferably, such beads have a weight average diameter of about 0.2 to about 5 mm, more preferably about 0.33 to about 1.5 mm, and still more preferably about 0.5 to about 1 mm. More preferably, substantially all of the spherical beads have a diameter of about 0.2 to about 5 mm, more preferably about 0.33 to about 1.5 mm, and still more preferably about 0.5 to about 1 mm. Without being bound by theory, it is generally believed that smaller grinding media are more efficient in the milling process of the invention since more bead-bead contact results.

The amount, by weight, of grinding media used to prepare nanoparticulate drug particles according to the process of the invention depends on the particular volume of liquid dispersion medium used, the drug used, the size, density and shape of the grinding media, and the size of the vessel in which the grinding takes place. The amount of grinding media can be readily optimized by one skilled in the art taking into account the above factors. Generally, a suitable suspension:grinding media weight ratio is about 1:10 to about 1:1, preferably about 2:10 to about 9:10 and more preferably about 4:10 to about 8:10. The suspension in this context includes all components of the liquid dispersion medium as well as the drug.

Milling Apparatus

A suitable milling apparatus for use in the process of the invention is illustrated diagrammatically in FIG. 1.

A vessel 11 is adapted to receive a suspension comprising the liquid dispersion medium 12 for the drug, grinding media 13 and magnetically activatable means 14 for stirring the dispersion medium with grinding media therein.

The vessel 11 is illustratively a vial having a capacity of about 0.1 ml to about 40 ml and preferably has a cover 15 to prevent spillage during milling. The vessel is held in place by suitable support means such as a clamp 16.

The grinding media 13 are illustratively spherical beads, about 0.2 mm to about 5 mm in diameter, and are illustratively of latex, glass or zirconium oxide.

The magnetically activatable means for stirring illustratively comprises a magnetic stir bar 14 which preferably comprises a high strength magnetic material, for example neodymium. An activating device 17, illustratively a magnetic stir plate, preferably with the cover plate removed to increase field strength, is placed near, preferably immediately under, the stirring means.

The term "magnetically activatable" as used herein with respect to the means for stirring describes a means for stirring which is capable of being set into motion by magnetic forces. To "magnetically activate" a means for stirring, as the phrase is used herein, describes use of a magnetic force to cause motion, preferably rotation, of the means for stirring.

Any suitable magnetically activatable means for stirring can be used in the process of the invention. A preferred magnetically activatable means for stirring is a magnetic stir bar or a rotating magnet. Magnetic stir bars and/or rotating magnets used as magnetically activatable means for stirring in processes of the invention can be of any suitable size and/or shape (e.g., oblong, oval, rectangular, cylindrical, egg-shaped, etc.) and can be uncoated or coated with any suitable material, for example rubber, plastic, metal, fluoropolymer, etc. Preferably, the magnetically activatable means for stirring is of sufficient magnetic strength so as to resist decoupling during the milling process. A sufficient strength of a magnetically activatable means for stirring will be determined based on, inter alia, viscosity of the liquid dispersion medium, amount of grinding media being used, desired milling speed, and vessel size. One or more magnetically activatable means for stirring can be used.

One illustrative commercially available stir bar suitable as a magnetically activatable means for stirring is a samarium-cobalt stir bar (Mastco). Such stir bars are available in egg-shape having longitudinal lengths of 10 mm, 15 mm, 25 mm, and larger.

In a particularly preferred embodiment, the stir bar is a high strength magnetic stir bar comprising (i) a non-reactive, abrasion-resistant case having a longitudinal axis; and (ii) a magnetic assembly comprising one to a plurality of lanthanide magnets completely enclosed in and substantially filling the case. Preferably the assembly has a coercive force and/or a maximum energy product substantially greater than that of a samarium-cobalt magnet, and has a polarity substantially aligned with the longitudinal axis of the case.

In a particularly preferred embodiment, the magnetic assembly comprises a plurality of lanthanide magnets linearly and contiguously arranged, each magnet having a first face in the orientation of a north pole and an opposing face in the orientation of a south pole. Adjoining faces of adjacent magnets have opposite polarity, and the first and second faces are substantially perpendicular to the longitudinal axis of the case.

Suitable lanthanide magnets can be of any desired shape, for example box- doughnut-, triangular-, bar- or disk-shape. Preferably the magnets are of disk- or doughnut-shape. Most preferably the magnets are of disk-shape. Where the magnets are of disk- or doughnut shape, they preferably have a diameter of about 2 to about 25 mm and a thickness of about 0.5 to about 20 mm. Where the stir bar comprises more than one magnet, it is preferred that all of the magnets have substantially the same shape and preferably, the individual faces present on each magnet are of substantially the same cross-sectional area. Preferably, each magnet has cross-sectional faces of substantially the same surface area as the other magnets.

Lanthanide magnets herein are magnets composed of a material comprising at least one lanthanide element. Preferably such magnets have a coercive force and/or a maximum energy product substantially greater than that of a samarium cobalt magnet. Particularly preferred lanthanide magnets comprise neodymium. Such magnets can comprise additional materials, for example iron and boron. An exemplary lanthanide magnet comprises neodymium/iron/boron, also referred herein as an NdFeB magnet.

A non-reactive, abrasion-resistant case herein can comprise any suitable material. Preferably, the material is water-impermeable, resistant to cracking or leaking during use in the process of the invention, and is chemically inert. The case can be a single-piece case or a multi-piece case. Non-limiting illustrative examples of suitable materials for use in such a case include rubber, metals, epoxy, plastics and other polymers, and combinations thereof. Illustrative polymers include RheFlex® tubing (Rheodyne), polypropylene, polymethylmethacrylate, fluoropolymers such as polytetrafluoroethylene (PTFE, available commercially as Teflon®), ethylene-tetrafluoroethylene fluoropolumer (e.g. Tefzel®), perfluoroalkoxy copolymer resin (Teflon® PFA), fluorinated ethylene propylene, polychlorotrifluoroethylene, polyvinylidene fluoride fluoroplastic (e.g. Kynar), etc. A particularly preferred case comprises PTFE tubing whereby the ends of the tube are fitted with PTFE discs and sealed with epoxy cement.

Figure 2:
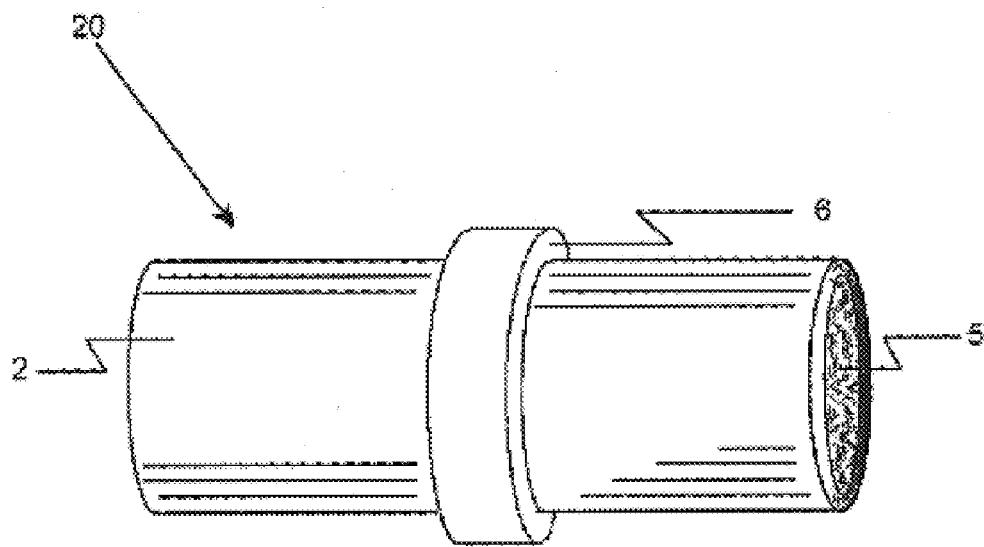
FIG. 2 shows a perspective representation of a high strength magnetic stir bar suitable for the process of the invention.
Figure 3:
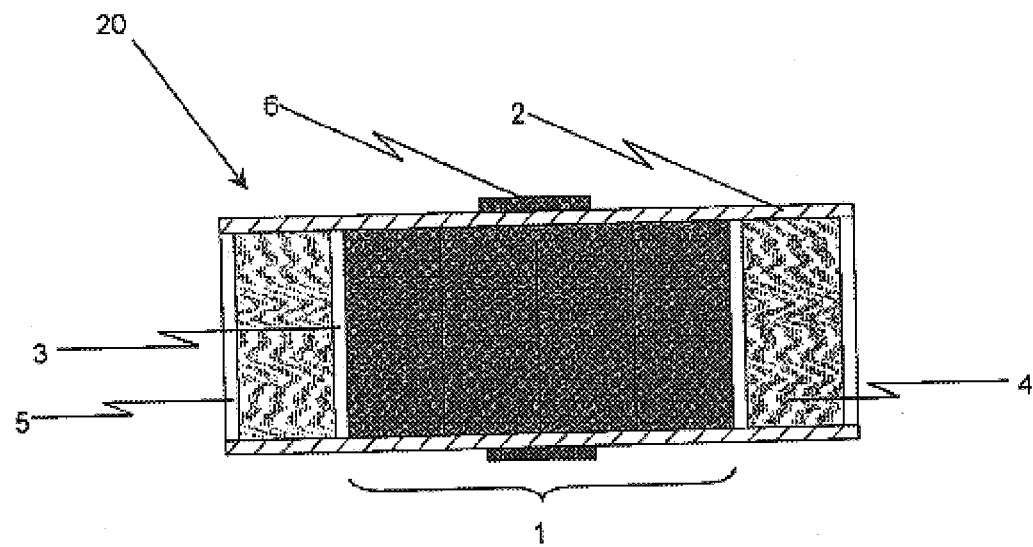
FIG. 3 shows a cross section view of a high strength magnetic stir bar suitable for the process of the invention.
Figure 4:
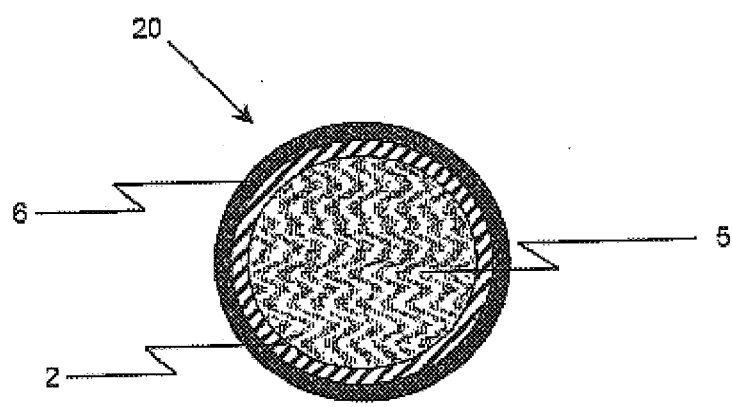
FIG. 4 shows a side view of a high strength magnetic stir bar suitable for the process of the invention.

An exemplary high strength magnetic stir bar 20 for use in a process of the invention is illustrated in FIG. 2 (perspective representation), FIG. 3 (section view), and FIG. 4 (side view). In this example, disc-shaped NdFeB magnets 1 are linearly stacked to a desired length and press fit into a piece of PTFE tubing 2 which is of slightly greater length than the stacked magnets. The ends of the tubing are then sealed by placing epoxy cement 3 in the end of the tube, press fitting a PTFE disk 4 thereon, and placing another layer of epoxy cement 5 on the outside of the PTFE disk. Alternatively, the ends of the sleeve can be sealed with epoxy cement and no PTFE disk. To reduce rotational friction, a piece of external tubing 6, for example Tygon tubing, can be slipped over the tube so that the bar balances evenly when placed on a flat, horizontal surface. Preferably such external tubing is of lesser length than the stir bar and is fixably located around the midsection of the stir bar, for example as illustrated in FIG. 2.

This high strength stir bar has at least two important advantages over conventional commercially available stir bars. First, the bar is very difficult to decouple during milling, thus allowing for greater milling speeds and consequent reduced processing time. Second, the wide size range of available NdFeB magnets allows for preparation of stir bars of any length (typically to a resolution of 1 mm). Such stir bars are useful in processes of the invention and in any other process which would benefit from use of a high strength, sturdy, inexpensive, and custom-sized stir bar.

Any suitable device can be used to magnetically activate the means for stirring. A preferred device is a rotating magnet, preferably a high strength rotating magnet. The step of magnetically activating the means for stirring is performed by placing the device (in the active or 'on' position) near the vessel. The term "near" as used herein to describe the distance between the vessel and the device, indicates a distance not greater than that from which the particular magnetically activatable means for stirring can be set in motion by the particular device used; such a distance will be determined both by characteristics of the particular means for stirring and by characteristics of the device used to activate the means for stirring. Generally, such a distance is not greater than about 2 meters, preferably not greater than about 1 meter, more preferably not greater than about 0.5 meter, and still more preferably not greater than about 0.33 meter. In practice, the distance will be as short as can conveniently be arranged, for example about 0.01 to about 0.1 meter. If the device used to magnetically active the means for stirring is a stir plate, for example a Magnestir, removal of the cover plate will enhance performance by increasing the available magnetic field.

Any suitable size and/or type of vessel, for example a scintillation vial, a cryogenic tube, a beaker, a flask, a conical tube, a cylinder, etc., can be used in the process of the invention. Preferably, the vessel is made of glass or Pyrex® and has a flat bottom. As will be discussed below, when milling at the microgram scale, the vessel is preferably made of hard plastic or latex which can be punctured using moderate force. Preferably, prior to milling, the vessel is about 20% to about 85%, more preferably about 25% to about 80%, and still more preferably about 30% to about 75% full, by total volume. Such a volume includes the grinding media, magnetically activatable means for stirring, drug, and liquid dispersion medium.

Stirring Time and Rate

All other factors being equal (e.g., bead size, bead amount, bead material, vessel size etc.), size of drug particles prepared according to a process of the invention is inversely related to stirring time (i.e., the longer the stirring time, the smaller will be the drug particles) and stirring rate (i.e., the faster the stirring rate over a given period of time, the smaller will be the drug particles). Any desired stirring rate and/or amount of stirring time can be employed. In practice, however, a sufficient milling time will be about 0.15 to about 72 hours, preferably about 0.15 to about 48 hours, and more preferably about 0.15 to about 24 hours. Generally, a suitable stirring rate will be about 10 to about 4000 rpm, and preferably about 100 to about 3500 rpm. Typically, where milling speeds greater than about 1500 rpm are desired, a high strength stir bar as described herein above will be needed in order to resist decoupling. In performing the process of the invention, one of ordinary skill can readily optimize stirring time and rate as well as other factors described herein above in order to prepare drug particles to a desired size range.

Separation of Grinding Media and Suspension

Grinding media and/or magnetically activatable means for stirring can be separated from a milled suspension prepared according to the process of the invention by any suitable means. Non-limiting examples of illustrative separation means include filtration, suction filtration, centrifugal filtration, extraction with a syringe or pipette, pouring off, physical removal (e.g., with tongs or a net), etc. Illustratively, the separation means can comprise removing the milled suspension from a milling vessel using a transfer pipette, for example a 1.5 ml Samco. Preferably the transfer pipette has an aperture small enough so grinding media present in the vessel will not be not be entrained by the pipette. Optionally, the grinding media can be washed/rinsed with fresh liquid dispersion medium to aid in recovery of drug particles. For enhanced drug recovery, multiple small volume washes are generally preferred to one large volume wash. Filtration and pipetting are preferred means for separating a milled suspension from grinding media and/or magnetically activatable means for stirring.

When the process of the invention is performed at very small scales, for example microgram scale, recovery of suspension can be as low as about 50% to about 75%. Without being bound by theory, this appears to result from surface tension which causes suspension to be retained by grinding media. In most cases this limitation is addressed by rinsing the beads with fresh vehicle. However, this rinsing also dilutes the suspension which, if high concentrations of drug are to be administered, may be impractical. Furthermore, making a 50% excess of suspension to compensate for the anticipated loss in compound may be unacceptable when only small quantities of drug are available.

In such cases, centrifugal filtration may be used to remove suspension from grinding media. Where centrifugal filtration is used to remove suspension from the milling vessel, the milling vessel should comprise a penetratable hard plastic as opposed to glass. Centrifugal filtration is performed by using a small gauge needle or similar object to pierce one to a small plurality of holes in the bottom of the milling vessel. Without being bound by theory, no suspension typically drains out of such holes by gravity because of the surface tension effects as noted above. The pierced vessel is then suspended over a receiver vessel and the two vessels are placed in a centrifuge. The vessels are then centrifuged for about 10 to about 60 seconds at about 100 to about 1000 rpm during which time the suspension is transferred from the milling vessel to the receiver vessel; the grinding media remain in the milling vessel. Preferably, the minimum amount centrifugation time and speed necessary to transfer suspension from the milling vessel to the revciever vessel should be used. Suspensions having high concentrations or viscosities may necessitate longer or faster spinning or the use of more holes. One of ordinary skill in the art will readily optimize centrifugation filtration conditions based on size and characteristics of the milled suspension.

Dilution

In one embodiment of the invention, a milled suspension resulting from step (c) or (d) of the above process is further diluted to form a pharmaceutical suspension. The milled suspension is preferably diluted with a liquid dispersion medium selected to minimize drug particle aggregation upon storage, for example as is described hereinabove. Any additional pharmaceutically acceptable excipients may also be added to the pharmaceutical suspension.

Drying

In a particularly preferred embodiment of the invention, a milled suspension resulting from step (c) or (d) of the above process is dried to form a drug powder. The drying step can comprise any suitable method of drying, for example evaporation, rotovapping (rotary evaporation), spray drying, lyophilization, conventional heating, for example in an oven, etc. Spray drying and rotovapping are preferred methods of drying. Any suitable spray drying method known in the art can be employed. Generally, spray drying is a process by which a solution or suspension comprising dissolved or dispersed drug is rapidly sprayed over a current of warm air, resulting in formation of a dry powder.

The drying step can occur prior to or after removal of grinding media and magnetically activatable means for stirring. Especially where the drying step comprises spray drying, grinding media and magnetically activatable means for stirring are preferably removed prior to drying.

Formulation

A drug powder prepared as provided herein can be further formulated together with one or more pharmaceutically acceptable excipients to produce a pharmaceutical composition, for example by direct compression or granulation. The term "excipient" herein means any substance, not itself a therapeutic agent, used as a carrier or vehicle for delivery of a therapeutic agent to a subject or added to a pharmaceutical composition to improve its handling, storage, disintegration, dispersion, dissolution, release or organoleptic properties or to permit or facilitate formation of a dose unit of the composition into a discrete article such as a capsule or tablet suitable for oral administration. Excipients include, by way of illustration and not limitation, diluents, disintegrants, binding agents, adhesives, wetting agents, lubricants, glidants, crystallization inhibitors, surface modifying agents, substances added to mask or counteract a disagreeable taste or odor, flavors, dyes, fragrances, and substances added to improve appearance of the composition.

Excipients employed in preparing compositions according to the invention can be solids, semi-solids, liquids or combinations thereof. Formulation can occur by any known technique of pharmacy that comprises admixing an excipient with the drug powder. A composition prepared by the process of the invention contains a desired amount of drug per dose unit and, if intended for oral administration, can be in the form, for example, of a tablet, a caplet, a pill, a hard or soft capsule, a lozenge, a cachet, a dispensable powder, granules, a suspension, an elixir, a liquid, or any other form reasonably adapted for such administration. If intended as an imbibable liquid, for example a suspension, elixir or a liquid, drug powder prepared according to the invention can be suspended in one or more inert carriers, for example water or fruit juice. If intended for parenteral administration, it can be in the form, for example, of a suspension. If intended for rectal administration, it can be in the form, for example, of a suppository. Presently preferred are oral dosage forms that are discrete dose units each containing a predetermined amount of drug, such as tablets or capsules.

EXAMPLES

The following examples illustrate aspects of the present invention but should not be construed as limitations.

Example 1

Dispersions D1–D4 containing 5% by weight celecoxib were prepared by the process described below. The dispersions differed only in the particle size range of the celecoxib.

1. Celecoxib was micronized in an air jet mill to form a drug powder.
2. The drug powder was added to an aqueous solution containing 2.5% low viscosity hydroxypropylcellulose (HPC-SL) and 0.12% sodium dodecyl sulfate, to form a suspension.
3. The suspension was wet milled to form a milled suspension according to the following protocol. A sample amount of 6.0 ml of the suspension (containing 20% celecoxib), a 19 mm magnetic stir bar made by VWR, 8 ml of lead-free glass beads, and 50 μl of antifoaming agent (Sigma Antifoam A Concentrate) were added to a 20 ml scintillation vial. To provide a milled suspension having a target particle size range of 6–7 μm (i.e., the size range achieved in the micronizing step, used to provide a comparative composition), the vial was shaken for two minutes. To provide a milled suspension having smaller target particle size ranges, the vial was suspended over a high-strength rotating magnet so that milling occurred by agitation of the glass beads by rotation of the magnetic stir bar. Target particle size ranges were varied by controlling magnet rotation rate, milling time and/or bead size, as shown in Table 1. Small aliquots were removed at intervals in order to monitor progress of particle size reduction.
4. The resulting milled suspension in each case was transferred to a larger vial and diluted with fresh vehicle to form a final milled suspension. Nominal celecoxib concentration in final suspensions was 5% by weight.

TABLE 1

Milling conditions used to produce milled suspensions D1–D4.

| Milled Suspension | Target size range (μm) | Bead size (mm) | Milling time (min) | Milling speed (rpm) |
|---|---|---|---|---|
| D1 | 6–7 | 3.3–3.6 | — | — |
| D2 | 1–3 | 3.3–3.6 | 26 | 900 |
| D3 | 0.5–0.9 | 1.25–1.55 | 25 | 900 |
| D4 | 0.2–0.4 | 0.5 | 52 | 1250 |

Example 2

Celecoxib particle size in milled suspensions D1–D4 as prepared in Example 1 was determined by laser (Fraunhofer) diffraction and by optical microscopy.

Figure 5:
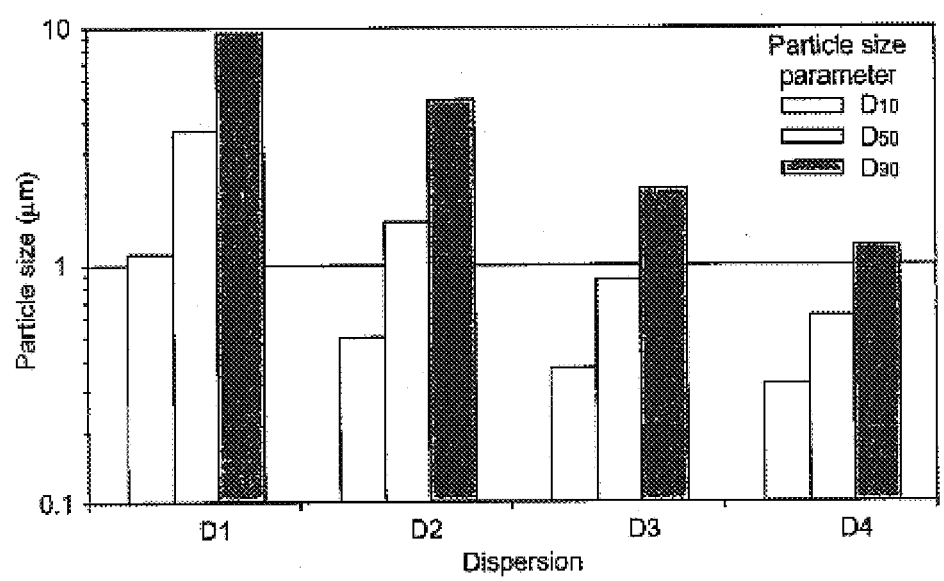
FIG. 5 presents particle size data for milled suspensions D1–D4 prepared as described in Example 1, as measured by Fraunhofer diffraction.

Fraunhofer scattering was measured on static suspensions samples using a Sympatec spectrometer. Samples were diluted with water into a static cell at a concentration that maintained a reduction in laser intensity of approximately 20%. The choice of collection lens was determined by the population of large material present in suspension, and thus was different for each sample. However, the smallest focal length optic appropriate was used in each case. No Mie scattering corrections were applied. The results, presented in FIG. 5, show a $D_{50}$ particle size consistent with the target size range. $D_{50}$ and other particle size parameters shown in FIG. 5 are believed to be overestimated for the 0.2–0.4 μm celecoxib dispersion, since this size range is at the very limit of detection by this technique.

Figure 6:
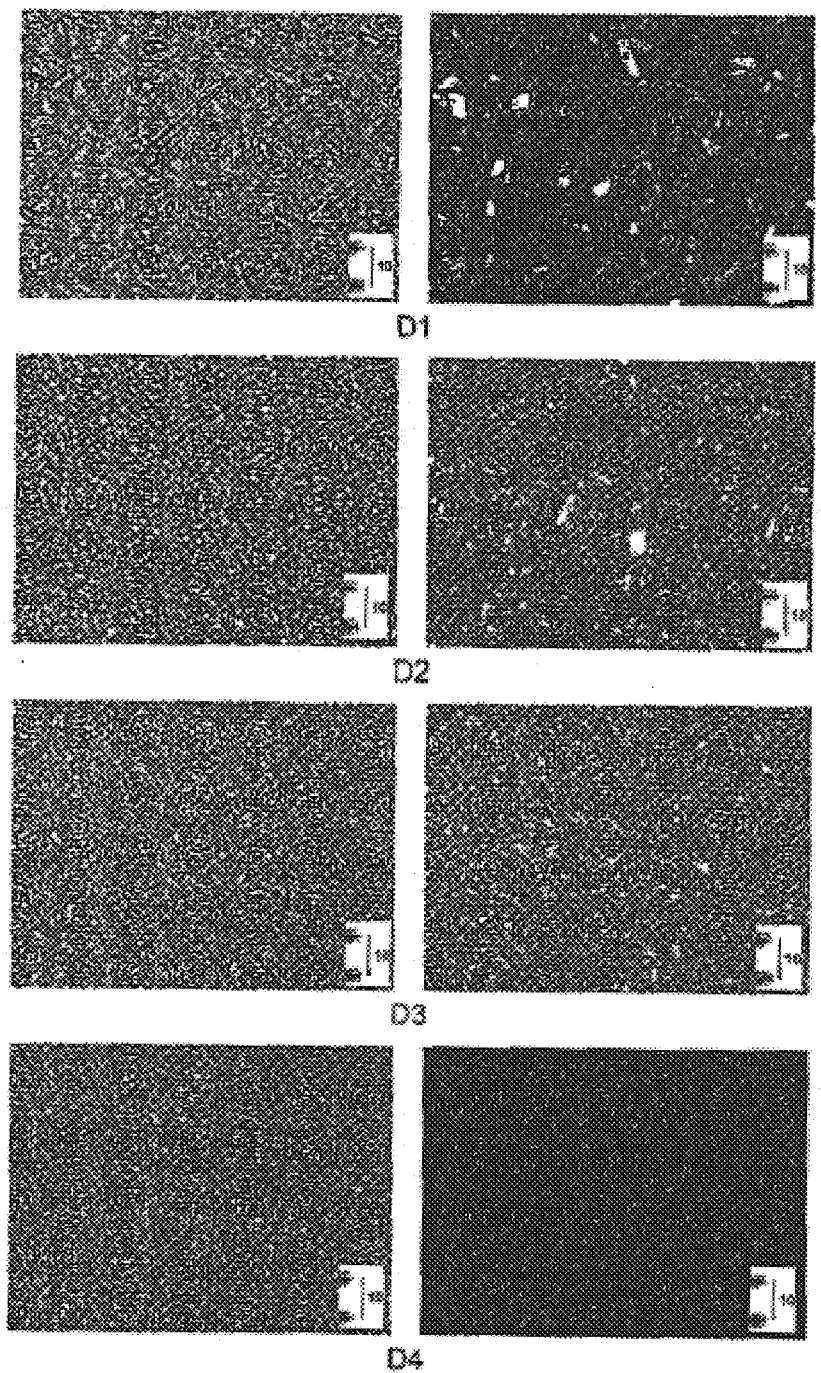
FIG. 6 shows optical micrographs of samples taken from milled suspensions D1–D4 under non-polarized (left) and polarized (right) light.

In order to visually confirm particle sizes, optical microscopy was used. Observations were carried out using an Olympus BH-2 microscope with attached video camera. Images were then digitized (Snappy 4.0; Play Inc., Rancho Cordova, Calif.) and manipulated (Paint Shop Pro 6.02; JASC, Eden Prairie, Minn.) as appropriate. FIG. 6 shows micrographs of samples taken from celecoxib dispersions D1–D4 with non-polarized (left) and polarized (right) light. The bar represents 10 μm. Significant Brownian motion was observed in suspensions D3 and D4, an observation consistent with presence of very small nanoparticles. In contrast, only slight Brownian motion was noted in dispersion D2 and none at all in suspension D1.

Example 3

Samples of milled suspensions prepared in Example 1 were dried individually by rotovapping according to the following procedure: 3 ml of each 5% celecoxib suspension was placed in a 10 ml recovery flask and attached to a conventional laboratory roto-evaporator (Buchi, RE11 Rotovapor). The flask was suspended in water at a temperature of 40° C. and rotated at approximately 100 rpm. A gentle vacuum was pulled on the flask for 0.5–1 hour to avoid bubbling of the suspension. After this time, a full house vacuum was employed and the evaporation proceeded for not less than 48 hours.

Example 4

Samples of milled suspensions prepared in Example 1 are spray dried individually at room temperature using a Yamato GB-21 spray dryer to form drug powders DP1, DP2, DP3 and DP4, respectively, under the following conditions: (a) liquid flow rate of 5 ml/min; (b) inlet air temperature of 110–130° C.; (c) outlet air temperature of 60–70° C., and (d) drying airflow of about 30% to about 50% of the capacity of the spray dryer.

Example 5

Valdecoxib, linezolid, phenytoin, griseofulvin and carbamazepine were milled according to the general procedure described for celecoxib in Example 1. Milling parameters are shown in Table 2.

TABLE 2

Milling parameters for various drugs

|  | Valdecoxib | Linezolid | Phenytoin |
|---|---|---|---|
| Solution Components | 2% PVP-K30 and 0.15% SDS in $H_2O$ | 2% PVP-K30 and 0.15% SDS in $H_2O$ | 3.75% PVP-K30; 0.5% SDS; 10 mM Na citrate pH 3 |
| Anti-foam (μl) | 3 | 30 | 40 |
| Drug Concentration (%) | 0.25 | 20 | 10 |
| Suspension volume (ml) or weight (g) | 0.5 g | 3 g | 7.5 ml |
| Stir bar type | NdFeB bar | NdFeB bar | NdFeB bar |
| Stir bar length (mm) | 5 | 3 | 19 |
| Grinding media size (mm) | 0.50–0.75 | 0.50–0.75 | 0.50–0.75 |
| Grinding media volume (ml) or weight (g) | 0.75 g | 4.7 g | 8.0 ml |
| Milling time (h) | 15 | 18 | 11 |
| Milling Speed (rpm) | 3000 | 3000 | 1500 |
| $D_{50}$ (nm) | 460[1] | 1900[1] 1000[2] | 200[1] 130[3] |

|  | Griseofulvin | Carbamazepine |
|---|---|---|
| Solution Components | 3.75% PVP-K30; 0.5% SDS; 10 mM Na citrate pH 3 | 3.75% PVP-K30; 0.5% SDS; 10 mM Na citrate pH 3 |
| Anti-foam (μl) | 40 | 40 |
| Drug Concentration (%) | 10 | 10 |
| Suspension volume (ml) or weight (g) | 7.5 ml | 7.5 ml |
| Stir bar type | NdFeB bar | NdFeB bar |
| Stir bar length (mm) | 19 | 19 |
| Grinding media size (mm) | 0.50–0.75 | 0.50–0.75 |
| Grinding media volume (ml) or weight (g) | 8.0 ml | 8.0 ml |
| Milling time (h) | 11 | 11 |
| Milling Speed (rpm) | 1500 | 1500 |
| $D_{50}$ (nm) | 250[1] 160[3] | 2500[1] 2600[3] |

Size Detection Method: [1]Turbidimetry, [2]Optical Microscopy, [3]X-Ray Diffraction.

What is claimed is:

1. A process for reducing particle size of a drug, the process comprising
   (a) dispersing about 10 g or less of the drug in a suitable volume of a liquid dispersion medium to form a suspension;
   (b) bringing together in a vessel grinding media, magnetically activatable means for stirring and the suspension, wherein the magnetically activatable means for stirring comprises a magnetic stir bar;
   (c) magnetically activating the means for stirring to effect milling of the suspension to a weight average particle size not greater than about 1 mm; and
   (d) separating the resulting milled suspension from the grinding media and the magnetically activatable means for stirring.

2. The process of claim 1 wherein about 5 g or less of the drug is dispersed in the liquid dispersion medium.

3. The process of claim 1 wherein about 2.5 g or less of the drug is dispersed in the liquid dispersion medium.

4. The process of claim 1 wherein the amount of liquid dispersion medium results, after the drug is dispersed therein, in a concentration of the drug in the liquid dispersion medium of about 0.1% to about 90% by weight.

5. The process of claim 1 wherein the amount of liquid dispersion medium results, after the drug is dispersed therein, in a concentration of the drug in the liquid dispersion medium of about 5% to about 65% by weight.

6. The process of claim 1 wherein the amount of liquid dispersion medium results, after the drug is dispersed therein, in a concentration of the drug in the liquid dispersion medium of about 10% to about 50% by weight.

7. The process of claim 1 wherein the liquid dispersion medium comprises water.

8. The process of claim 7 wherein the liquid dispersion medium further comprises at least one surface modifying agent.

9. The process of claim 8 wherein the at least one surface modifying agent is present in a total amount of about 0.1% to about 90% by weight based on the combined weight of the drug and the at least one surface modifying agent.

10. The process of claim 8 wherein the at least one surface modifying agent is present in a total amount of about 0.1% to about 50% by weight based on the combined weight of the drug and the at least one surface modifying agent.

11. The process of claim 8 wherein the at least one surface modifying agent is present in a total amount of about 0.1% to about 25% by weight based on the combined weight of the drug and the at least one surface modifying agent.

12. The process of claim 8 wherein at least one surface modifying agent is selected from the group consisting of sodium dodecyl sulfate, polyvinylpyrrolidone, hydroxypropylmethylcellulose, and hydroxypropylcellulose.

13. The process of claim 8 wherein the liquid dispersion medium further comprises at least one antifoaming agent.

14. The process of claim 13 wherein the at least one antifoaming agent comprises a silicon-based polymer.

15. The process of claim 14 wherein the at least one antifoaming agent is selected from the group consisting of simethicone, Sigma® Antifoam A, and equivalents thereto.

16. The process of claim 8 wherein the at least one antifoaming agent is present in the liquid dispersion medium in a total amount of about 0.001% to about 2.5%, by weight.

17. The process of claim 8 wherein the at least one antifoaming agent is present in the liquid dispersion medium in a total amount of about 0.003% to about 1%, by weight.

18. The process of claim 1 wherein the liquid dispersion medium comprises a non-aqueous solvent.

19. The process of claim 1 wherein the grinding media comprise a material selected from the group consisting of glass, lead-free glass, zirconium oxide and latex.

20. The process of claim 1 wherein the grinding media comprise lead-free glass.

21. The process of claim 20 wherein the sphere-shaped grinding media have a weight average diameter of about 0.5 to about 1 mm.

22. The process of claim 1 wherein at least a substantial portion of said grinding media are in the shape of a sphere.

23. The process of claim 22 wherein said sphere-shaped grinding media have a weight average diameter of about 0.2 to about 5 mm.

24. The process of claim 22 wherein said sphere-shaped grinding media have a weight average diameter of about 0.33 to about 1.5 mm.

25. The process of claim 1 wherein the weight ratio of the suspension to all of said grinding media is about 1:10 to about 1:1.

26. The process of claim 1 wherein the weight ratio of the suspension to all of said grinding media is about 2:10 to about 9:10.

27. The process of claim 1 wherein the weight ratio of the suspension to all of said grinding media is about 4:10 to about 8:10.

28. The process of claim 1 wherein the magnetically activatable means for stirring comprises a high strength magnetic stir bar.

29. The process of claim 28 wherein the high strength magnetic stir bar comprises one to a plurality of magnets, wherein each of the magnets comprises neodymium.

30. The process of claim 28 wherein the high strength magnetic stir bar comprises one to a plurality of NdFeB magnets.

31. The process of claim 1 wherein said step (c) is performed by placing a rotating magnet near the vessel.

32. The process of claim 1 wherein said step (c) is performed until substantially all of the drug particles have been reduced to a size not greater than about 1 mm.

33. The process of claim 1 wherein said step (c) is performed until the drug particles have been reduced to a weight average particle size of about 10 to about 1000 nm.

34. The process of claim 1 wherein said step (c) is performed until the drug particles have been reduced to a weight average particle size of about 100 to about 1000 nm.

35. The process of claim 1 wherein said step (c) is performed until the drug particles have been reduced to a weight average particle size of about 400 to about 900 nm.

36. The process of claim 1 wherein said step (c) is performed until the drug particles have been reduced to a weight average particle size of about 500 to about 900 nm.

37. The process of claim 1 wherein said separation step (d) comprises filtration.

38. The process of claim 1 wherein said filtration step (d) comprises centrifugal filtration.

39. The process of claim 1 wherein said separation step (d) comprises removal of the suspension from the milling vessel with a pipette.

40. The process of claim 1 further comprising diluting the milled suspension with at least one pharmaceutically acceptable excipient to form a pharmaceutical suspension.

41. The process of claim 1 further comprising drying the milled suspension to form a drug powder.

42. The process of claim 41 wherein the drying step is performed by evaporation, spray drying, rotovapping, lyophilization, or heating in an oven.

43. The process of claim 41 further comprising mixing the drug powder together with one or more excipients to form a powder blend.

44. The process of claim 41 further comprising compressing or encapsulating the powder blend to form a solid dosage form.

45. The process of claim 41 further comprising granulating the powder blend to form a granulate prior to compressing or encapsulating.

46. The process of claim 45 wherein granulating is performed by wet granulation to form a wet granulate, and wherein the wet granulate is dried prior to compressing or encapsulating.

47. The process of claim 41 further comprising suspending the drug powder in an inert liquid vehicle to form an imbibable liquid.

48. The process of claim 47 wherein the inert liquid vehicle is water or fruit juice.

49. A process for reducing particle size of a drug of low water solubility, the process comprising
  (a) dispersing about 10 g or less of the drug in a suitable volume of a liquid dispersion medium to form a suspension;
  (b) bringing together in a vessel grinding media, magnetically activatable means for stirring and the suspension, wherein the magnetically activatable means for stirring comprises a magnetic stir bar;
  (c) magnetically activating the means for stirring to effect milling of the suspension to a weight average particle size not greater than about 1 mm; and
  (d) separating the resulting milled suspension from the grinding media and the magnetically activatable means for stirring.

* * * * *